United States Patent
Ueno

(10) Patent No.: US 9,477,794 B2
(45) Date of Patent: Oct. 25, 2016

(54) SIMULATION METHOD FOR HIGH POLYMER MATERIAL

(71) Applicant: Sumitomo Rubber Industries, Ltd., Kobe-shi, Hyogo (JP)

(72) Inventor: Shinichi Ueno, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 34 days.

(21) Appl. No.: 13/859,035

(22) Filed: Apr. 9, 2013

(65) Prior Publication Data

US 2013/0311155 A1 Nov. 21, 2013

(30) Foreign Application Priority Data

May 16, 2012 (JP) ................. 2012-112678

(51) Int. Cl.
| | |
|---|---|
| *G06F 17/50* | (2006.01) |
| *C08L 21/00* | (2006.01) |
| *G01N 33/44* | (2006.01) |
| *G06F 19/00* | (2011.01) |

(52) U.S. Cl.
CPC ......... *G06F 17/5009* (2013.01); *G06F 19/704* (2013.01); *C08L 21/00* (2013.01); *C08L 2666/02* (2013.01); *G01N 33/445* (2013.01); *G06F 17/5095* (2013.01); *G06F 19/701* (2013.01)

(58) Field of Classification Search
None
See application file for complete search history.

(56) References Cited

FOREIGN PATENT DOCUMENTS

JP 2006-64658 A 3/2006

OTHER PUBLICATIONS

D. Brown, et al., "Effect of Filler Particle Size on the Properties of Model Nanocomposites", Macromolecules, vol. 41, (2008), pp. 1499-1511.*
J. Liu, et al "Nanoparticle Dispersion and Aggregation in Polymer Nanocomposites: Insights from Molecular Dynamics Simulation," Langmuir, vol. 27(12), Jun. 21, 2011, pp. 7926-7933.*
T. Desai, et al., "Molecular Dynamics Simulations of Polymer Transport in Nanocomposites", Journal of Chemical Physics, vol. 122, (2005), pp. 134910-1 through 134910-8.*
H. Yagyu, et al., "Coarse grained Molecular Dynamics Simulation of Nanofilled Crosslinked Rubber," Computation Materials Science, vol. 46, 2009, pp. 286 292.*

(Continued)

*Primary Examiner* — Kamini S Shah
*Assistant Examiner* — David M Rogers
(74) *Attorney, Agent, or Firm* — Birch, Stewart, Kolasch & Birch, LLP

(57) ABSTRACT

A computerized simulation method for evaluating the dispersion of fillers in a high polymer material is disclosed. The method comprises: a simulation step in which, using filler models and polymer models placed in a predetermined virtual space, a molecular dynamics calculation is performed; and an evaluation step in which, from results of the simulation step, the dispersion of the filler models is evaluated. The evaluation step includes a step of computing a mean-square displacement of most influential particles for which a cutoff distance largest in the filler particle is defined. Thereby, the dispersion can be evaluated certainly at short times.

4 Claims, 10 Drawing Sheets

(56) References Cited

OTHER PUBLICATIONS

K. Hagita, "Coarse grained Molecular Dynamics Simulation Approach for Polymer Nano Composites Rubber," Published On-line in 2009 at: http://www.issp.u-tokyo.ac.jp/super/invited/Hagita2009.pdf.*

W. Jorgensen, et al., "Optimized Intermolecular Potential Functions for Liquid Hydrocarbons," Journal of the American Chemical Society, vol. 106, 1984, pp. 6638 6646.*

Allegra et al., "Theories and simulations of polymer-based nanocomposites: From chain statistics to reinforcement," Progress in Polymer Science, vol. 33, 2008 (available online Mar. 4, 2008), pp. 683-731, XP023906890.

Brown et al., "Effect of Filler Particle Size on the Properties of Model Nanocomposites," Macromolecules, vol. 41, No. 4, 2008 (published on Web Jan. 25, 2008), pp. 1499-1511, XP055082941.

Extended European Search Report for European Application No. 13163174.9, dated Oct. 17, 2013.

Raos et al., "Nonequilibrium simulations of filled polymer networks: Searching for the origins of reinforcement and nonlinearity," The Journal of Chemical Physics, vol. 134, 2011 (published online Feb. 1, 2011), pp. 054902-1-054902-14, XP009172858.

* cited by examiner

SIMULATION METHOD FOR HIGH POLYMER MATERIAL

BACKGROUND OF THE INVENTION

The present invention relates to a simulation method for a high polymer material capable of simulating and evaluating the dispersion of fillers in a high polymer material certainly at short times.

High polymer materials such as compounded rubber used in vehicle tires usually contain fillers such as carbon black and silica. It is well known in the art that the dispersion of fillers in a compounded rubber exerts a strong influence on properties, e.g. strength of the rubber.

In recent years, in order to evaluate the dispersion of fillers in a high polymer material, various computerized simulation (numerical calculation) methods have been proposed.

In this kind of simulation method, filler models of fillers and polymer models of a high polymer material are defined, and a molecular dynamics (MD) calculation is performed on the filler models and polymer models placed or set in a predetermined virtual space.

Then, based on results of the simulation, the dispersion of the fillers is evaluated by an operating personnel. Thus, it is difficult to provide objective exact evaluations.

Further, it takes a long time to compute the movements of the filler models in order to simulate the filler dispersion.

SUMMARY OF THE INVENTION

It is therefore, an object of the present invention to provide a computerized simulation method for evaluating the dispersion of fillers in a high polymer material, by which the filler dispersion state can be simulated and evaluated certainly at short times.

According to the present invention, a computerized simulation method for evaluating the dispersion of fillers in a high polymer material comprises:

a filler model defining step in which filler models of the fillers are defined, wherein each of the filler models represents a plurality of filler particles;

a polymer model defining step in which polymer models of the high polymer material are defined, wherein each of the polymer models represents one or more polymer particles;

a simulation step in which a molecular dynamics calculation is performed for the polymer models and the filler models placed in a predetermined virtual space; and an evaluation step in which the state of dispersion of the filler models is evaluated from results obtained through the simulation step, wherein between the particles inclusive of the filler particles and the polymer particles, potentials such that when the distance between the concerned particles is decreased under a predefined cutoff distance, a mutual interaction occurs therebetween, are defined, one of the filler particles in each filler model is defined as a most influential particle for which a largest cutoff distance is defined, and the evaluation step includes a step in which a mean-square displacement of the most influential particles is computed.

The method according to the present invention may be provided with the following features (I)-(III):
(I) the filler particles of each filler model are a single center filler particle and at least four surface filler particles whose centers are positioned on a spherical surface whose center coincides with a center of the center filler particle, equilibrium lengths are respectively defined between the center filler particle and the surface filler particles and between the surface filler particles, and
the center filler particle is the most influential particle;
(II) the cutoff distance between the center filler particles is larger than the sum of the radius of the above-mentioned spherical surface and the cutoff distance between the surface filler particles;
(III) the evaluation step includes a step in which the mean-square displacement is computed at five or more time intervals.

Therefore, in a filler model, a potential from the outside of the filler model acts on the most influential particle prior to any other filler particles. In the molecular dynamics calculation, the most influential particle is taken as the representative point of the filler model. If migrations of the most influential particles are increased, the filler models can be considered as being dispersed widely.

From the mean-square displacement, the extent of a movement of a most influential particle per unit time is obtained.

Accordingly, the dispersion of the filler models can be grasped, therefore, the filler dispersion state can be evaluated reliably at short times.

DESCRIPTION OF THE PREFERRED EMBODIMENTS

An embodiment of present invention will now be described in detail in conjunction with accompanying drawings.

The simulation method according to the present invention is a method for simulating and evaluating the dispersion of fillers in a high polymer material by the use of a computer 1. Here, the term "high polymer material" is intended to include at least rubber, resin and elastomer.

The term "filler" is intended to include at least carbon black, silica and alumina.

Figure 1:
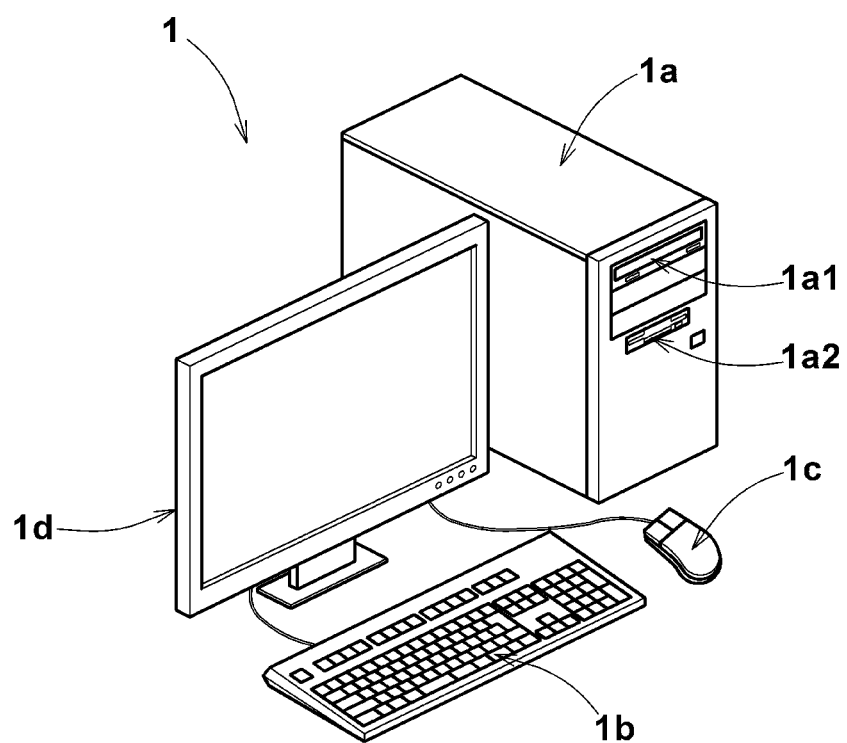
FIG. 1 is a perspective view of a computer system implementing a simulation method as an embodiment of the present invention.

As shown in FIG. 1 for example, the computer 1 comprises a main body 1a, a keyboard 1b, a mouse 1c and a display 1d. The main body 1a comprises an arithmetic processing unit (CPU), ROM, work memory, storage devices such as magnetic disk, disk drives 1a1 and 1a2 and the like. In the storage device, programs/software for carrying out the simulating method are stored.

Figure 2:
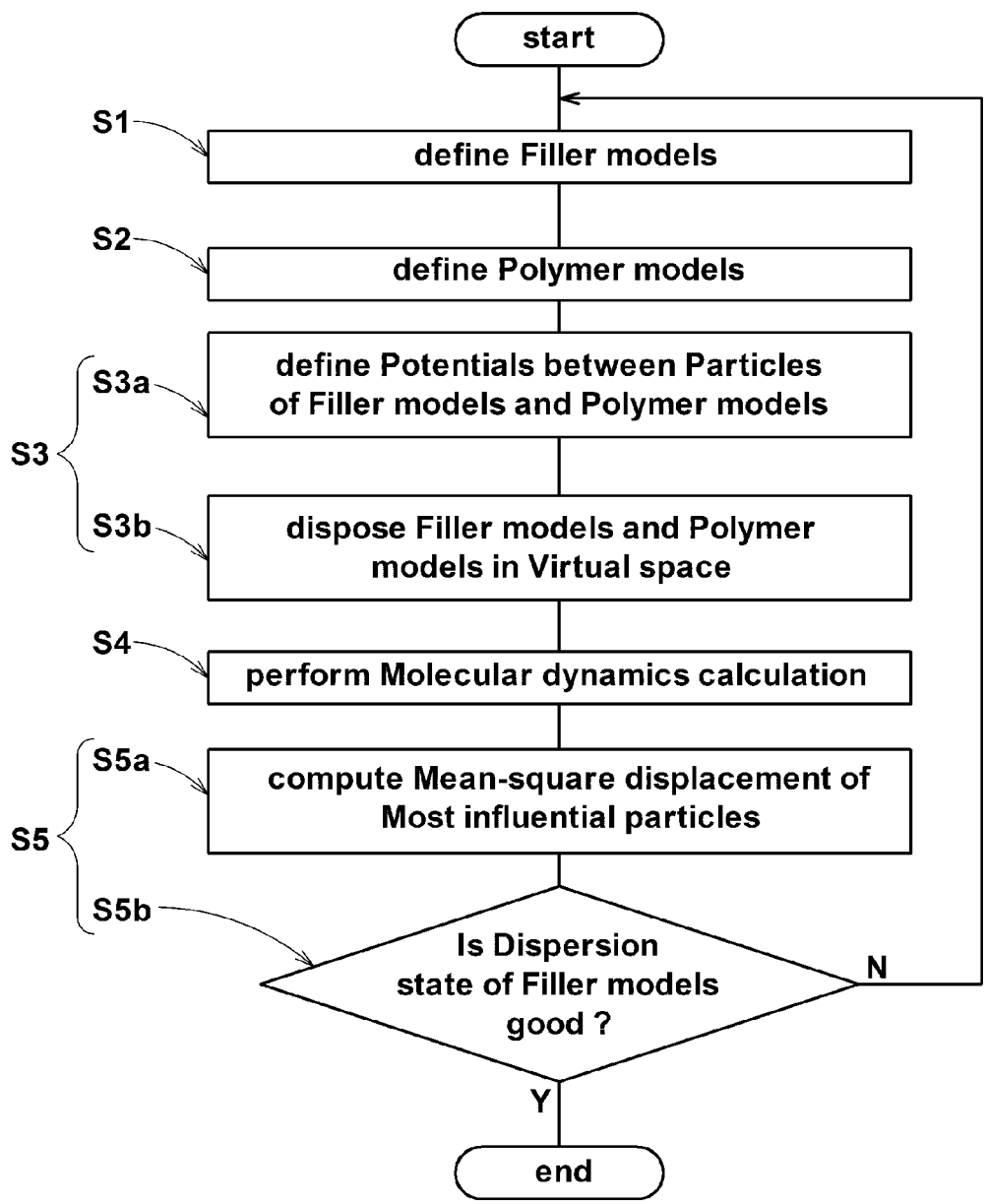
FIG. 2 is a flow chart of the simulation method in this embodiment.

FIG. 2 is a flowchart of the simulation method as an embodiment of the present invention.

Figure 3:
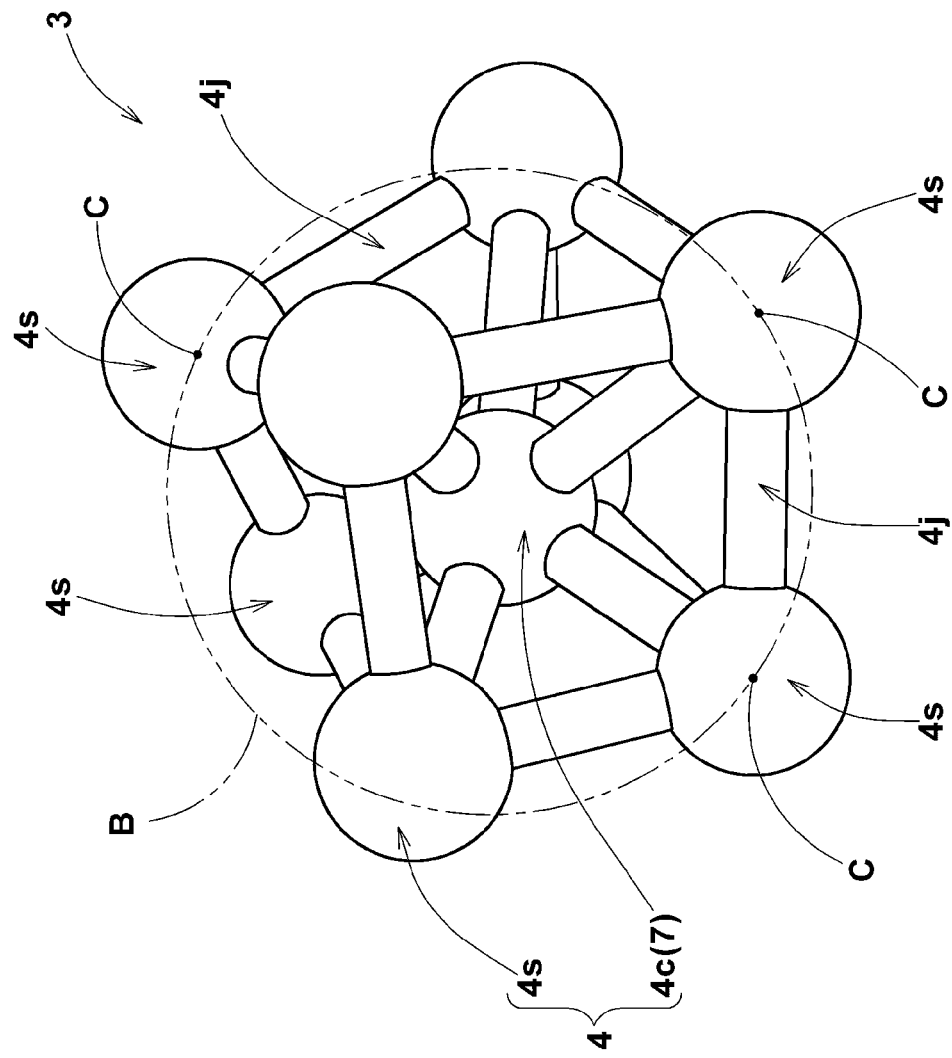
FIG. 3 is a diagram showing a filler model.

In this method, firstly, a filler model defining step S1 is implemented. In this step S1, as shown in FIG. 3, filler models 3 of the fillers are defined, wherein each filler model 3 is defined to represent a plurality of filler particles 4 (e.g. carbon particles), and the filler particle 4 is a sphere having a certain diameter.

Incidentally, the filler model 3 corresponds to numerical data (inclusive of the mass, volume, diameter and initial coordinates of each of the filler particles 4) necessary to deal with the fillers by the molecular dynamics. Such numerical data are entered and stored in the computer 1.

The filler particles 4 constituting each filler model 3 are a single center filler particle 4c, and at least four in this example eight surface filler particles 4s, wherein the centers C of the surface filler particles 4s are positioned on a spherical surface B of which center coincides with the center of the center filler particle 4c.

In each filler model 3, between the center filler particle 4c and the surface filler particles 4s and also between the surface filler particles 4s, there are provided joining chains 4j on which equilibrium lengths are respectively defined.

Here, the equilibrium lengths are the bond distances between the center filler particle 4c and the surface filler particles 4s and between the surface filler particles 4s when the relative positions of the surface filler particle 4s on the spherical surface B become steady.

If the bond distance is changed, it revert to the equilibrium length by the joining chain 4j so as to become a steady state.

In the filler model 3 in this example, the center filler particle 4c and the surface filler particles 4s are bonded, keeping their relative positions. Further, the center filler particle 4c and three or more surface filler particles 4s in each filler model 3 are arranged so as not to locate in the same plane or one plane. The surface filler particles 4s are positioned at the vertices of a polyhedron, and the center filler particle 4c is positioned at the center of the polyhedron.

Next, polymer models 5 of the high polymer material are defined. (step s2)

Figure 4:
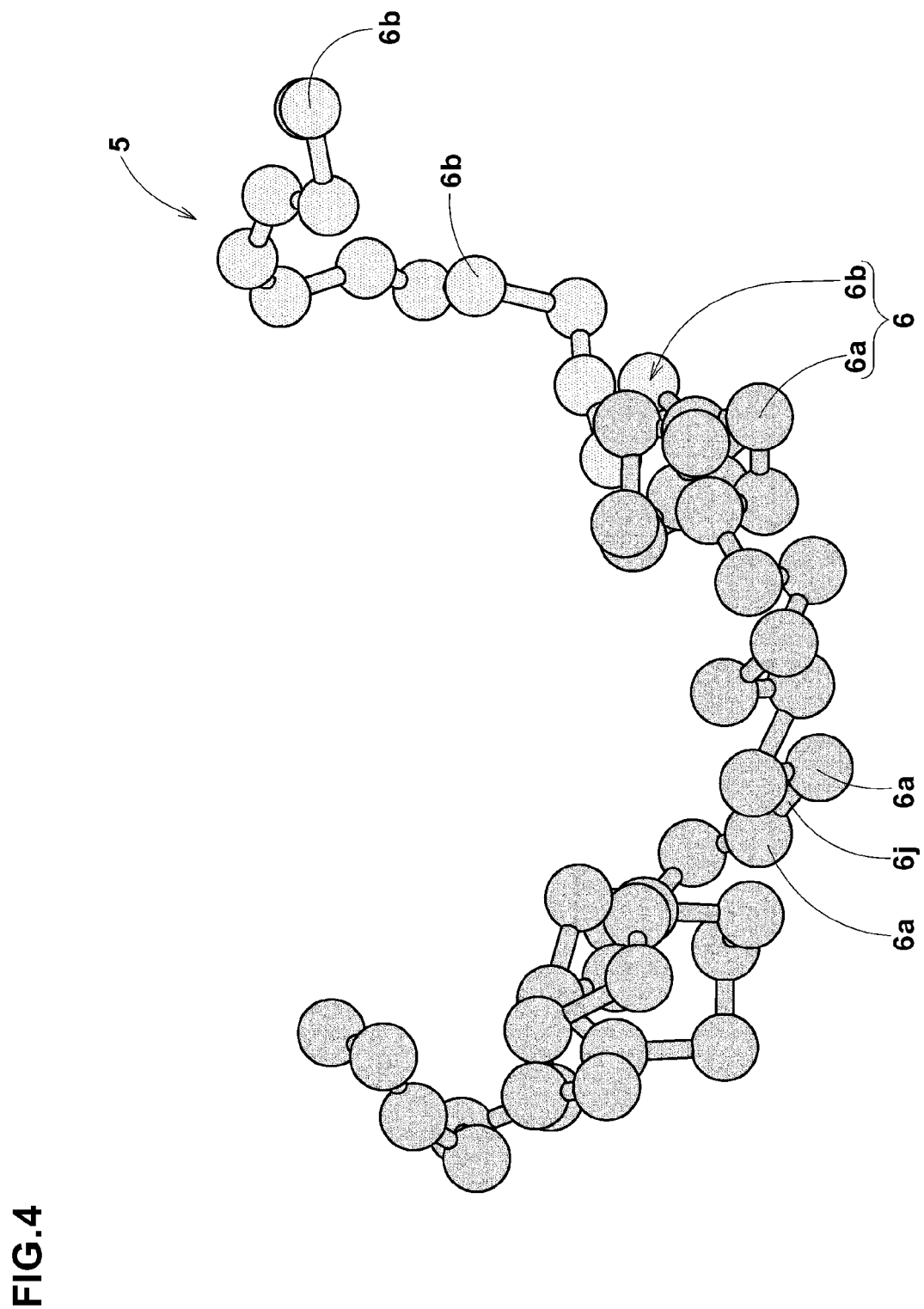
FIG. 4 is a diagram showing a polymer model.

In this step S2, as shown in FIG. 4, each polymer model 5 is defined to represent at least one polymer particle 6 preferably a plurality of polymer particles 6 of the high polymer material.

Incidentally, the polymer model 5 corresponds to numerical data necessary to deal with the high polymer material by the molecular dynamics. Such numerical data are entered and stored in the computer 1.

The polymer particles 6 of the polymer model 5 in this example include modified basal particles 6b and nonmodified particles 6a, and different potentials (after-mentioned) are defined for the particles 6a and particles 6b.

Each of the particles 6a and 6b is a sphere having a certain diameter.

Between the particles 6a and 6b, there are provided joining chains 6j so as to keep them under restraint and to have a three dimensional structure like a straight-chain polymer.

Next, a simulation condition setting step S3 is implemented.

In the step S3, simulation conditions necessary for executing the subsequent molecular dynamics (MD) calculation are set. In this embodiment, firstly, a potential defining step S3a is implemented.

Figure 5:
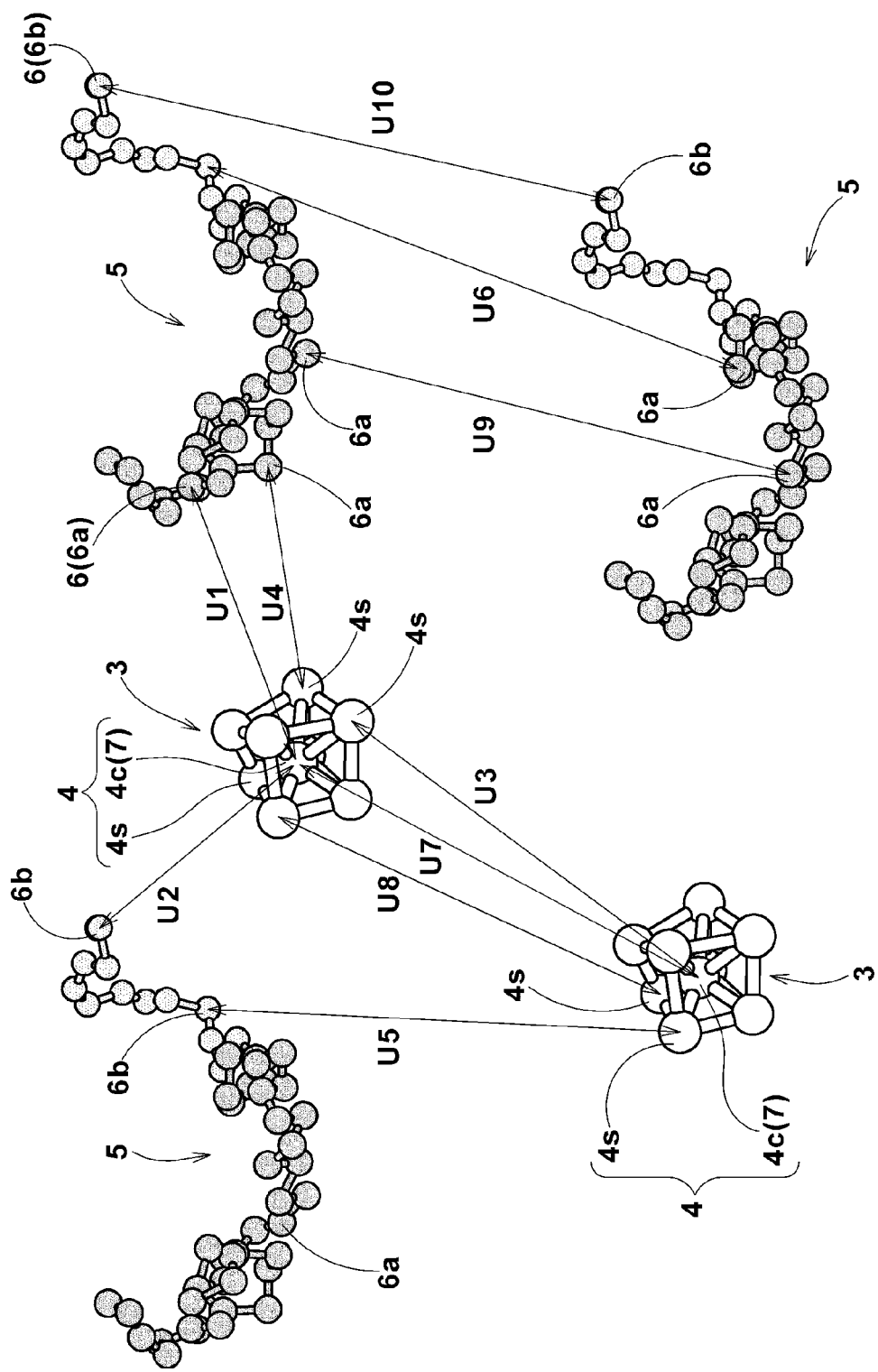
FIG. 5 is a diagram for explaining potentials of the filler particles and polymer particles.

In this step S3a, as shown in FIG. 5, potentials are respectively defined between the filler particles 4c, 4s of a filler model 3 and the filler particles 4c, 4s of another filler model 3, between the filler particles 4c, 4s of a filler model 3 and the polymer particles 6a, 6b of a polymer model 5, and between the polymer particles 6a, 6b of a polymer model 5 and the polymer particles 6a, 6b of another polymer model 5.

The potentials are stored in the computer 1 as numerical data, and used to calculate a force between the two particles concerned. Here, the potential is a function of the distance between the concerned particles. The potential U is given by the following expression (1):

$$U = a_{ij}(1 - r_{ij}/r_c)^2/2$$

where
- $a_{ij}$ is an invariable corresponding to the strength of the potential u defined between the particles concerned,
- $r_{ij}$ is the distance between the centers of the particles concerned, and
- $r_c$ is the cutoff distance predefined between the particles concerned.

with the expression (1), the potential u is defined such that a mutual interaction (in this embodiment, a repulsive force) occurs if the distance $r_{ij}$ is decreased under the predefined cutoff distance $r_c$. If the distance $r_{ij}$ is more than the cutoff distance $r_c$, the potential u is zero and no repulsive force occurs between the particles.

In this particular example, for the following combinations of two particles, potentials u1-u10 are defined:
- particles 4c-6a: potential u1
- particles 4c-6b: potential u2
- particles 4c-4s: potential u3
- particles 4s-6a: potential u4
- particles 4s-6b: potential u5
- particles 6a-6b: potential u6
- particles 4c-4c: potential u7
- particles 4s-4s: potential u8
- particles 6a-6a: potential u9
- particles 6b-6b: potential u10

As to the strength $a_{ij}$ of the potential, a treatise (J. Chem Phys. 107(11) 4423-4435 (1997)) proposes that the strength $a_{ij}$ of potential between particles of the same kind is set to be 25.

But, various researches made afterward (for example, Macromolecule vol. 39 6744(2006)) suggest that the strength $a_{ij}$ of potential between particles of the same kind is set to be 50, and the strength $a_{ij}$ of potential between particles of the different kinds is set to be 72.

In this example, by reference to these values, the strength $a_{ij}$ of the potentials u1-u10 are set as follows.
- potential u1: $a_{ij}=72$
- potential u2: $a_{ij}=25$
- potential u3: $a_{ij}=50$
- potential u4: $a_{ij}=72$
- potential u5: $a_{ij}=25$
- potential u6: $a_{ij}=72$
- potential u7: $a_{ij}=50$
- potential u8: $a_{ij}=50$
- potential u9: $a_{ij}=50$
- potential u10: $a_{ij}=50$ As above, the strength $a_{ij}(=25)$ of the potential u2, u5 between the modified basal particle 6b of the polymer model 5 and the filler particle 4c, 4s of the filler model 3 is set to be smaller than the strength $a_{ij}(=72)$ of the potential u1, u4 between the nonmodified particle 6a of the polymer particle 6 and the filler particle 4c, 4s of the filler model 3, therefore, in comparison with the nonmodified particle 6a, the modified basal particle 6b is decreased in the repulsive force.

Such modified basal particle 6b is increased in the affinity to the filler particle 4c, 4s, and therefore can simulate a denaturizing agent actually added in the high polymer material. Accordingly, by incorporating such modified basal particles 6b in the polymer model 5, the dispersion of the filler models 3 in the polymer models 5 can be changed, and it becomes possible to simulate a modified polymer.

In the expression (1), the cutoff distance $r_c$ is defined for each of the potentials u1-u10 as follows.

potential u1: $r_c$=3
potential u2: $r_c$=3
potential u3: $r_c$=3
potential u4: $r_c$=1
potential u5: $r_c$=1
potential u6: $r_c$=1
potential u7: $r_c$=5
potential u8: $r_c$=1
potential u9: $r_c$=1
potential u10: $r_c$=1

According to the present invention, one of the filler particles 4 of each filler model 3 is defined as a most influential particle 7.

Further, the following three different cutoff distances $r_c$ are predefined:

a largest cutoff distance used between the most influential particle 7 of a filler model 3 and the most influential particle 7 of another filler model 3;

a smallest cutoff distance used between any particle 4 other than the most influential particle 7 of a filler model 3 and any particle 4 other than the most influential particle 7 of another filler model 3; and a middle cutoff distance used between the most influential particle 7 of a filler model 3 and any particle 4 other than the most influential particle 7 of another filler model 3.

In this embodiment, the center filler particle 4c of each filler model 3 is defined as the most influential particle 7. Therefore, the cutoff distance $r_c$ used for the potential (for example u7) between the center filler particle 4c of a filler models 3 and the center filler particle 4c of another filler model 3 is set to be larger than the cutoff distance $r_c$ used for the potential (for example, u8) between the surface filler particle 4s of a filler model 3 and the surface filler particle 4s of another filler model 3.

The most influential particle 7 is a filler particle relating to the largest cutoff distance. Therefore, in a filler model 3, a potential from the outside of the filler model 3 acts on the most influential particle 7 (center filler particle 4c) prior to any other filler particles (surface filler particles 4s). Accordingly, the most influential particle 7 of the filler model 3 influences the motion of the filler model 3. Therefore, in the molecular dynamics calculation, it is possible to take the most influential particle 7 as the representative point of the filler model 3.

If migrations of the most influential particles 7 are increased, the filler models 3 are considered as being dispersed widely.

Figure 6:
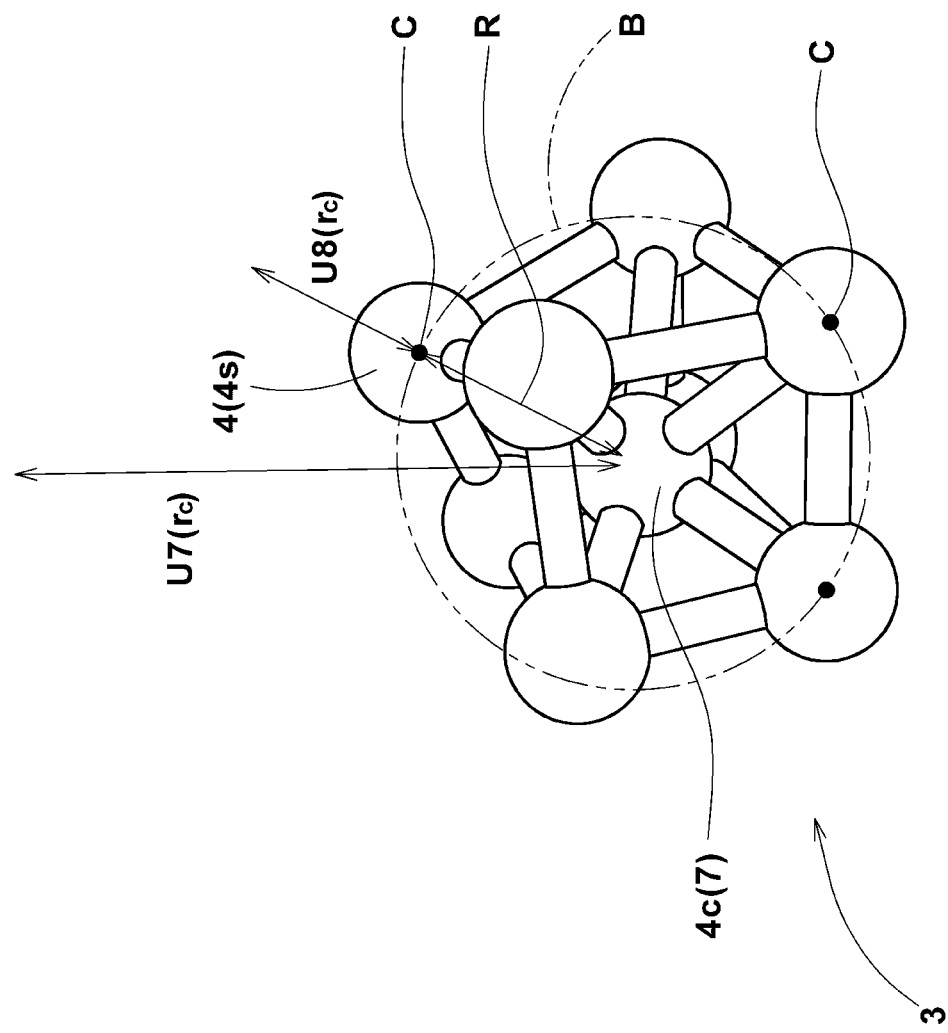
FIG. 6 is a diagram for explaining the cutoff distance of a filler particle.

It is desirable that, as shown in FIG. 6, the large cutoff distance $r_c$ (potential u7) used between the most influential particles 7 and 7 (i.e. between the center filler particles 4c and 4c) is set to be more than the sum ($r_c$+R) of the small cutoff distance $r_c$ (potential u8) between the particles 4 other than the most influential particle 7 (i.e. the surface filler particles 4s and 4s) and the radius R of the above-mentioned spherical surface B in order to assure that the potential acts on the most influential particle 7 prior to any other filler particles.

Between the most influential particles 7, the potential acts radially. Therefore, in the molecular dynamics calculation, the computer 1 can treat the filler models 3 as spheres like the actual filler.

Figure 7:
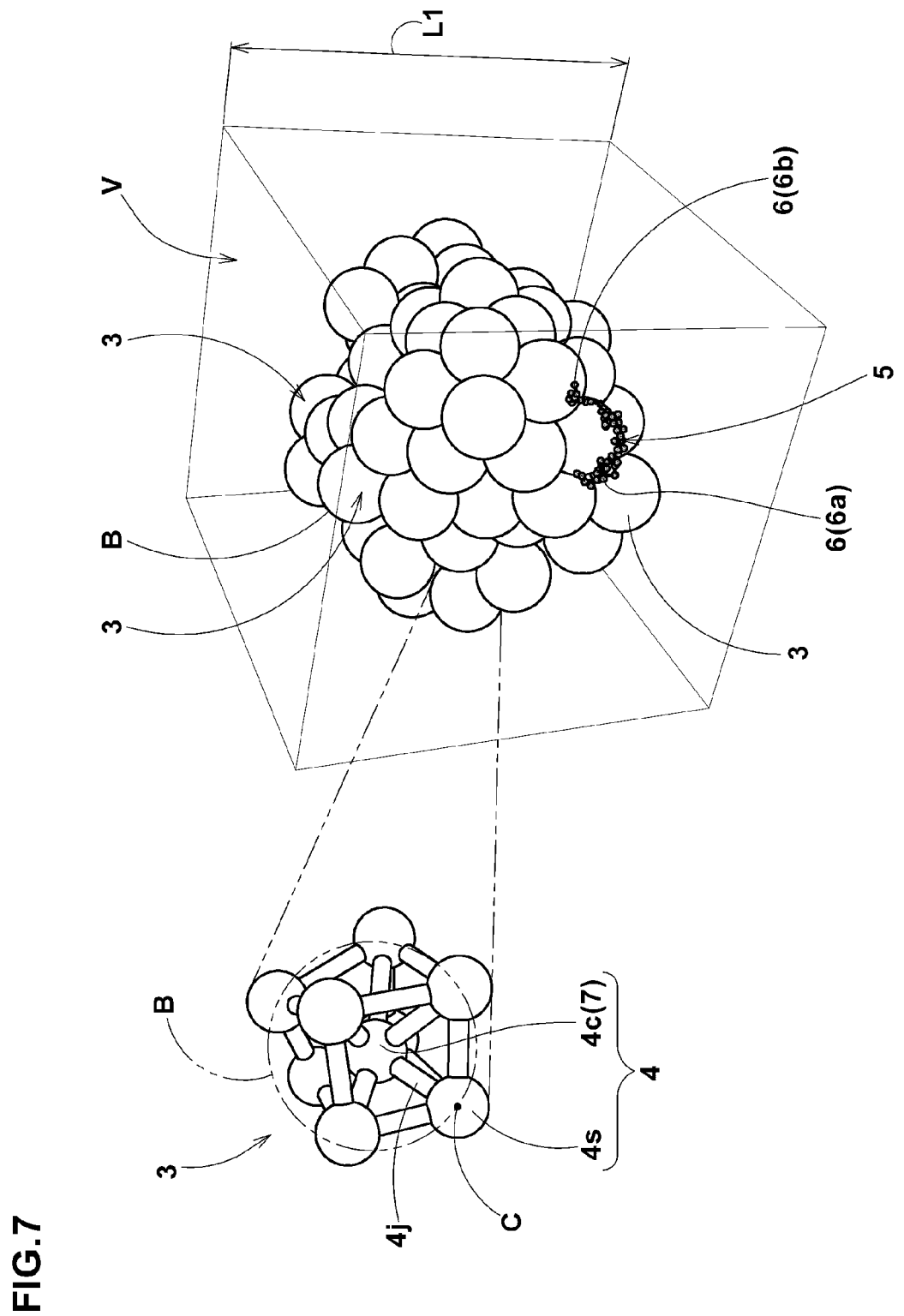
FIG. 7 is a perspective diagram for explaining a virtual space in which filler models and polymer models are disposed.

Next, a step s3b is implemented, wherein, as shown in FIG. 7, a virtual space v having a predetermined volume is defined and the filler models 3 and the polymer models 5 are disposed in the virtual space v.

The virtual space v corresponds to a minute fraction of the actual high polymer material, e.g. polymer as the analysis object.

In this embodiment, the shape of the virtual space v is a regular hexahedron whose each side has a length L1 of from 20 to 40 [σ] for example. [σ] is unit of length. In the virtual space, for example, 500 to 1500 filler models 3 and 1000 to 3000 polymer models 5 are initially randomly disposed.

Next, a simulation step s4 is implemented. In this step S4, a molecular dynamics calculation is performed.

In the molecular dynamics calculation, assuming that all of the filler models 3 and the polymer models 5 in the virtual space V follow the classical dynamics, the calculation is made according to Newton's equation of motion for a given time period, and the motion of each of the filler particles 4c and 4s and the polymer particles 6a and 6b is tracked at each time step during the time period.

In this embodiment, the molecular dynamics calculation is continued until the initial placement of the filler models 3 and polymer models 5 which is artificial, becomes not artificial (structure relaxation).

As an example, when the number of the time steps reaches to a predetermined number (for example 500 to 300000), the molecular dynamics calculation is ended.

During making the molecular dynamics calculation, the number of all the particles existing in the system or the virtual space 8 and the volume and temperature of the system are kept constant.

Next, an evaluation step s5 is implemented.

In this step S5, from results obtained in the simulation step S4, the dispersion state of the filler models 3 is evaluated. For this, firstly, a step S5a is implemented. In this step, the mean-square displacement of the most influential particles 7 to be evaluated is computed.

The mean-square displacement (MSD) is given by the following expression (2):

$$MSD = <|r(t)-r(0)|^2> \quad (2)$$

where
r(0) is the coordinate of the center 7c of a most influential particle at a given time point,
r(t) is the coordinate of the center 7c of the most influential particle at a time interval of length t after the given time point, and
< . . . > denotes an ensemble average over the predetermined most influential particles 7 and over some time intervals.

Figure 8:
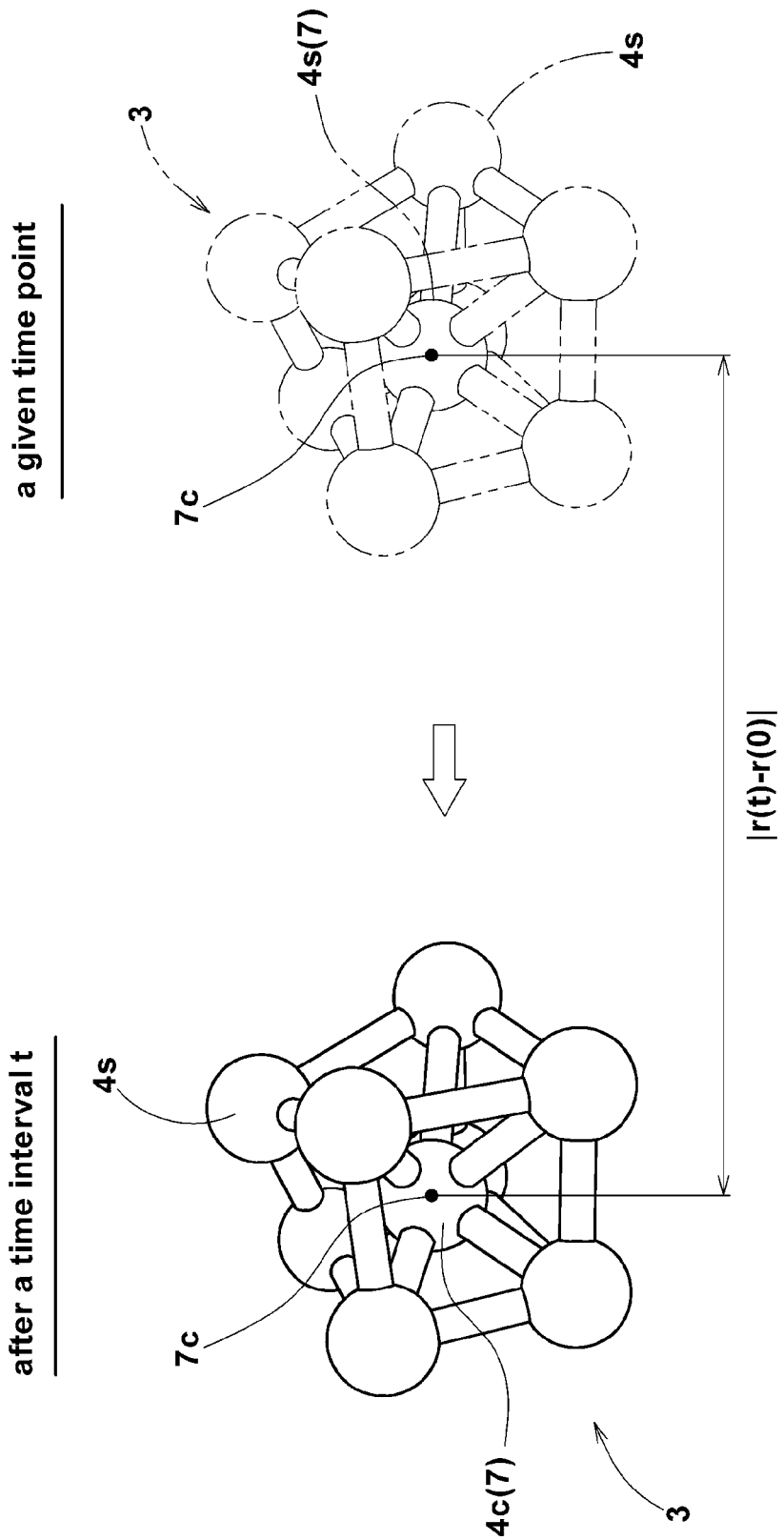
FIG. 8 is a diagram for explaining the extent of a movement of a filler particle.

In the expression (2), |r(t)−r(0)| is the (vector) distance traveled by the most influential particle 7 over the time interval of length t as shown in FIG. 8.

The obtaining of the value of the MSD allows to grasp the extent of a movement of the most influential particle 7.

As noted above, in the molecular dynamics calculation, the most influential particle 7 is taken as the representative point of the filler model 3.

Therefore, from the value of the MSD, the extent of a movement of the filler model 3 can be grasped.

Figure 9:
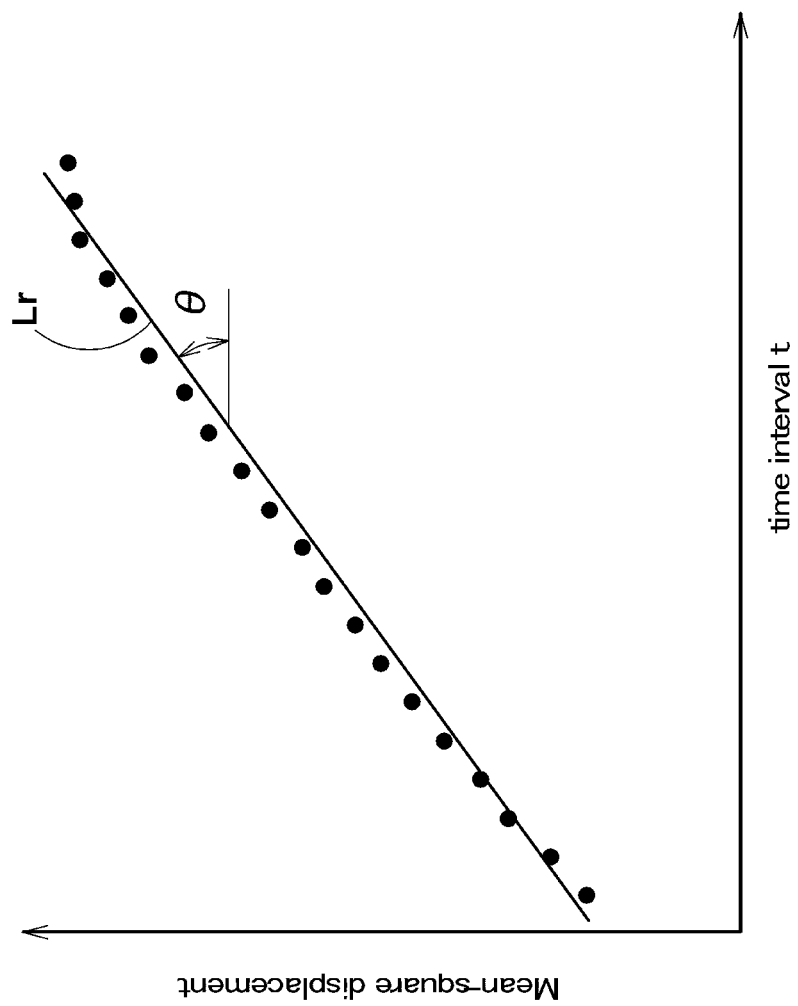
FIG. 9 is an exemplary graph of the mean-square displacement of most influential particles.

FIG. 9 shows an exemplary graph in which the values of the mean-square displacement computed at some time intervals, are plotted.

From the slope θ of the regression line Lr to the mean-square displacement, the self-diffusion coefficient of the most influential particle 7 can be obtained.

With the increase in the self-diffusion coefficient, the extent of a movement of the most influential particle 7 is increased. Therefore, based on whether the self-diffusion coefficient is large or nor, it is possible to judge whether the dispersion state of the filler models 3 is good or not. Thus, the dispersion state can be evaluated.

In FIG. 9, the mean-square displacement of the most influential particle 7 is increased in proportion to the increase in the time such increase means that the extent of the movement is wide, namely, the dispersion is good.

In this way, without the need for computing the mean-square displacement of the surface filler particle 4s, the dispersion of the filler model 3 can be evaluated and grasped certainly at short times.

For that purpose, it is desirable that the mean-square displacement is computed at at least five time intervals.

In other words, the number of plotted data is at least five (In the example shown in FIG. 9, the number is 20).

If the number is less than five, it is difficult to obtain the self-diffusion coefficient accurately, and there is a possibility that the dispersion state can not be grasped exactly. If the number exceeds 1000, the computational time increases. Therefore, the number of the time intervals is preferably set in a range of not less than 10 but not more than 100.

Next, a step s5b is implemented. In this step s5b, the computer 1 judges whether the dispersion state of the filler models 3 is good or not, based on whether the obtained mean-square displacement is within a predetermined acceptable range or not.

In this embodiment, if the dispersion state of the filler models 3 is judged as good, the simulation is ended.

On the other hand, if the dispersion state is judged as not good, taking the obtained mean-square displacement into consideration, the conditions previously set on the filler models 3 and the polymer models 5 are changed, and again the simulation is implemented. Such operation is repeated to find out conditions in which the filler models 3 are well dispersed.

Comparison Tests

Figure 10:
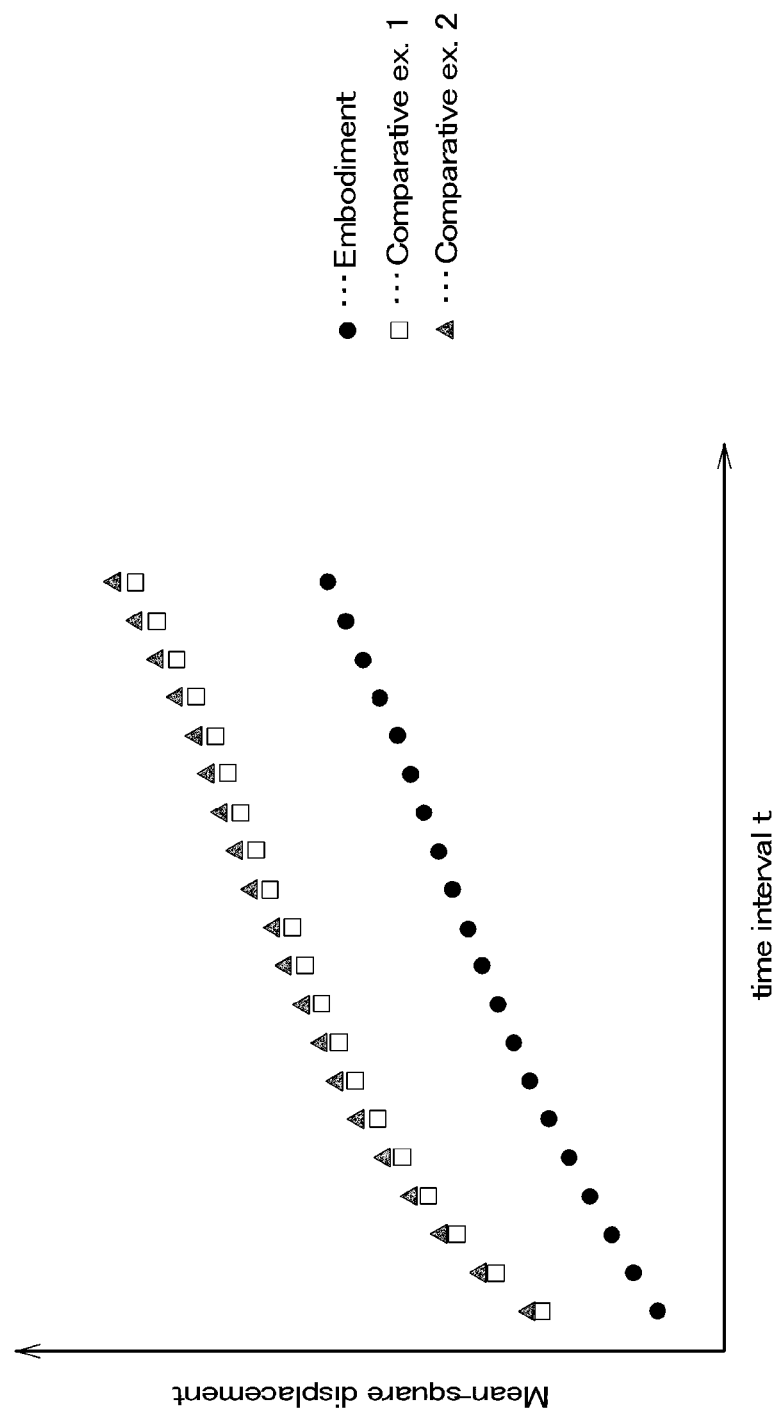
FIG. 10 is a graph in which the mean-square displacement computed by various methods are plotted.

According to the flowchart shown in FIG. 2, a molecular dynamics calculation on the filler models and polymer models was performed. Then, the mean-square displacement of the most influential particles, namely the center filler particles of the filler models, was computed. The result is shown in FIG. 10 as Embodiment.

Further, for comparison, the mean-square displacement of all of the filler particles of the filler models was computed. The result is shown in FIG. 10 as Comparative example 1.

Furthermore, the mean-square displacement of all of the surface filler particles of the filler models was computed. The result is shown in FIG. 10 as Comparative example 2.

The details of the filler models, polymer models and potentials were as described above. Other common specifications are as follows:
The length L1 of each side of the virtual space was 30 [σ].
The number of the filler models in the virtual space was 100.
The number of the polymer models in the virtual space was 1500.

The number of the time steps of the molecular dynamics calculation was 100000.

The mean-square displacement was computed at twenty time intervals.

In addition, without using the positions of the filler particles obtained in the molecular dynamics calculation as above, the positions of the gravity points of the respective filler models were computed, and the mean-square displacement of the gravity points was computed. (as Experimental example in Table 1)

Then, with respect to the mean-square displacement, the Embodiment, Comparative example 1, Comparative example 2 and Experimental example were compared. The results are shown in Table 1.

Further, as to the computational time, embodiment, comparative example 1, comparative example 2 and experimental example were compared. The results are shown in Table 1.

TABLE 1

| Method | Experimental example | Embodiment | Comparative example 1 | Comparative example 2 |
|---|---|---|---|---|
| Mean-square displacement | 1.08 | 1.05 | 3.01 | 3.48 |
| Computational time (hour) | 9.90 | 1.10 | 9.88 | 8.75 |

From the comparison of the mean-square displacement, it was confirmed that the Embodiment can simulate the filler dispersion state close to that by the Experimental example, therefore, a reliable evaluation is possible.

Further, in the Embodiment, it was not necessary to compute the gravity points as in the Experimental example, therefore, the computational time was remarkably reduced.

The invention claimed is:

1. A computerized simulation method for evaluating the dispersion of fillers in a high polymer material comprising:
    defining filler models of the fillers, wherein each of the filler models represents a plurality of filler particles which are a single most influential particle and at least four surface particles of which centers are positioned on a spherical surface whose center coincides with a center of said single most influential particle;
    defining polymer models of the high polymer material, wherein each of the polymer models represents one or more polymer particles;
    defining potentials between particles which are the filler particles and the polymer particles, wherein
        each potential is a function of a distance between the centers of the particles, and defined as causing a mutual interaction between the particles when the distance is decreased under a predefined cutoff distance,
        a largest cutoff distance is defined for the single most influential particle, and
        a cutoff distance smaller than said largest cutoff distance is defined for each of the surface particles;
    defining an equilibrium length between the single most influential particle and each of the surface particles in each of the filler models;
    defining an equilibrium length between the surface particles in each of the filler models;
    performing a molecular dynamics calculation for the polymer models and the filler models placed in a predetermined virtual space; and evaluating a state of dispersion of the filler models from results obtained through the molecular dynamics calculation, wherein
  a mean-square displacement of each of the filler models is obtained by computing a mean-square displacement of the single most influential particle without computing a mean-square displacement of each of the surface particles, and
  the state of dispersion of the filler models is evaluated based on the obtained mean-square displacements of the filler models,
wherein a cutoff distance between the single most influential particles of two of the filler models is larger than the sum of the radius of the above-mentioned spherical surface and a cutoff distance between the surface particles of the two of the filler models,
wherein the defining the potentials between particles includes:
  defining the largest cutoff distance between the most influential particle of a filler model and the most influential particle of another filler model;
  defining a smallest cutoff distance between any particle other than the most influential particle of a filler model and any particle other than the most influential particle of another filler model; and
  defining a middle cutoff distance between the most influential particle of a filler model and any particle other than the most influential particle of another filler model.

2. The simulation method according to claim 1, wherein the mean-square displacement is computed at five or more time intervals.

3. The simulation method according to claim 1, wherein the function defining the potential between the particles is given by $$U = a_{ij}(1 - r_{ij}/r_c)^2/2$$

wherein
  U is the potential,
  $a_{ij}$ is an invariable corresponding to the strength of the potential U,
  $r_{ij}$ is the distance between the centers of the particles, and
  $r_c$ is the cutoff distance between the particles.

4. The simulation method according to claim 3, wherein the evaluating the state of dispersion includes obtaining a self-diffusion coefficient of the most influential particles.

* * * * *